United States Patent [19]

Kawai et al.

[11] Patent Number: 4,511,305
[45] Date of Patent: Apr. 16, 1985

[54] MANIPULATOR

[75] Inventors: Seiji Kawai, Tokyo; Dairiku Matsumoto, Higashi minemachi, both of Japan

[73] Assignee: Meidensha Electric Mfg. Co., Ltd., Tokyo, Japan

[21] Appl. No.: 457,590

[22] Filed: Jan. 13, 1983

[30] Foreign Application Priority Data

Jan. 16, 1982 [JP] Japan ................................. 57-5105

[51] Int. Cl.$^3$ ............................................. B66C 1/10
[52] U.S. Cl. ..................................... 414/755; 901/29
[58] Field of Search ............... 414/735, 7, 4, 732; 901/19–29; 3/1.1, 12

[56] References Cited

U.S. PATENT DOCUMENTS 3,952,880  4/1976  Hill et al. ........................ 901/29 X
4,000,819  1/1977  Germond et al. .................... 414/7

FOREIGN PATENT DOCUMENTS 2378612  8/1978  France ............................... 414/7
 512048  6/1976  U.S.S.R. ........................... 901/29

Primary Examiner—Robert J. Spar
Assistant Examiner—Donald W. Underwood

[57] ABSTRACT

A manipulator of the type where a base and a hand are connected via a flexible arm in which the flexible arm comprises a plurality of hollow coupling members which are coupled to each other via universal joints in a manner allowing free flexion and integral rotation. Plural hand-operating shafts are attached to the center of the flexible arm via spherical bearings in a manner to allow relative rotation therebetween and coupled to each other via universal joints at intermediate points of the coupling members, and one of the hand-operating shafts is expandable. Actuators are housed inside the base to drive and rotate the flexible arm and hand-operating shafts, and a separate actuator is housed inside the base to flex the flexible arm.

3 Claims, 3 Drawing Figures

MANIPULATOR

BACKGROUND OF THE INVENTION

The present invention relates to an improvement for a manipulator and aims at minimizing the size of the part which acts as a wrist of a hand and at enhancing the reliability thereof.

Manipulators of a robot type or a fixed type have been utilized widely in operation in adverse environments, for handling dangerous objects, or in places too small for operators to conduct work, and they have been used for refined and complicated work.

In the structure of such a manipulator, the part which corresponds to the wrist of a human arm is driven to rotate or flex by an actuator provided within a body, of the device; however, as the driving mechanism for a hand equivalent, or more particularly the part which acts as fingers should be positioned ahead of the wrist member, the size of the wrist member unavoidably increases to the level where it is difficult to be inserted into a narrow part, thereby restricting the scope of application.

There has been proposed an arrangement where flexible wires or ropes are wired through the arm or wrist so as to drive the hand equivalent from inside the body; they have been found deterimental in reliability because proper operation can not be secured due to the expansion or sag of the wire or rope or they tend to become torn or worn easily. This may lead to accidents.

SUMMARY OF THE INVENTION

The object of the present invention is to provide a manipulator of a higher reliability and which is simple in operation of a wrist portion.

Another object of the present invention is to provide a manipulator which is so compact in the wrist portion as to be operable in narrow places.

Still another object of the present invention is to provide a manipulator which has the same function as a human being in the wrist and arm portions thereof and which is free of any restrictions in operation.

Still another object of the present invention is to provide a manipulator wherein driving mechanisms in the arm and wrist portions are integrated so as to simplify wirings as well as to facilitate manufacturing and maintenance.

In order to attain such purposes, the manipulator according to the present invention is of the type that a base and a hand are connected via a flexible arm, and is characterized in that said flexible arm comprises a plural number of hollow coupling members which are connected to each other via a universal joint and are freely flexible as well as integrally rotatable, that a plural number of hand operating shafts are provided at the center of said flexible arm via spherical bearings in a manner to allow relative rotation which are coupled to each other via a universal joint at the intermediate part of said coupling members while one of the hand operating shafts is made expandable, that said flexible arms and hand operating shafts are actuated by actuators housed in said base and that a separate actuator which flexes said flexible arms is provided within said base.

BRIEF DESCRIPTION OF THE DRAWINGS

FIG. 1 shows the flexed state and
FIG. 2 the stretched state.

DETAILED DESCRIPTION OF A PREFERRED EMBODIMENT

The present invention will now be described in detail referring to one embodiment shown in the attached drawings.

Figure 1:
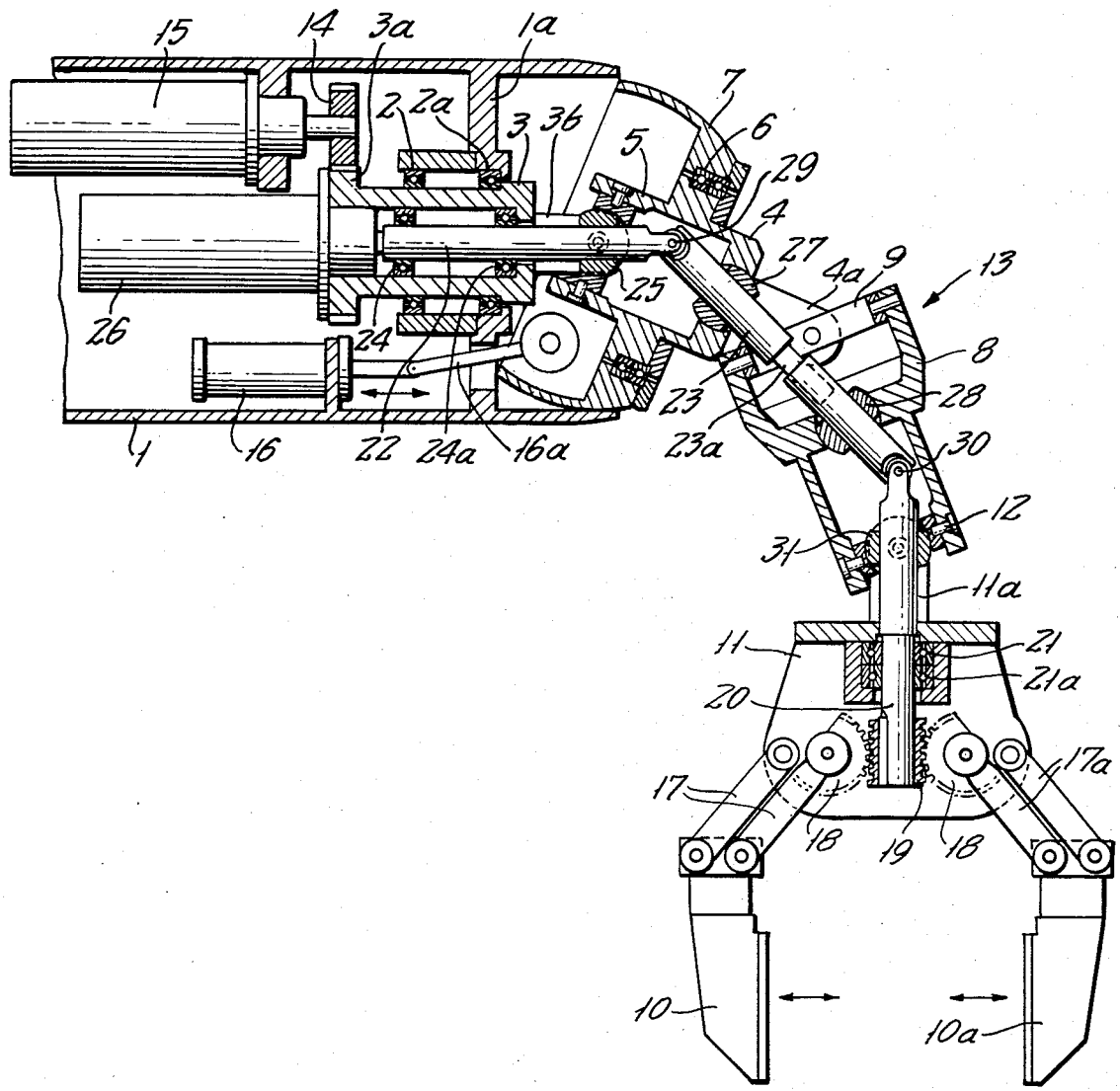
FIGS. 1 and 2 are vertical cross-sectional views of the arm of an embodiment of the manipulator according to the present invention.
Figure 2:
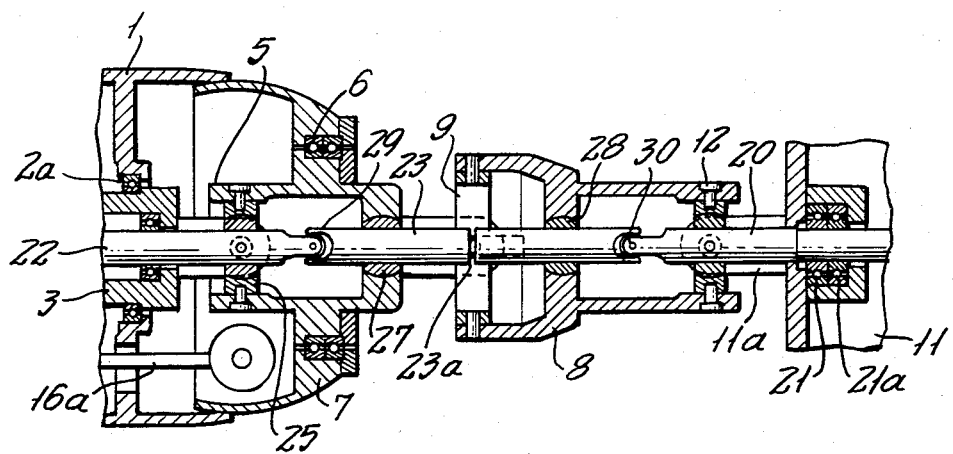

FIGS. 1 and 2 are vertical cross-sectional views to show an embodiment of the manipulator according to the present invention: FIG. 1 indicates the flexed state thereof and FIG. 2 the extended state.

Two bearings 2, 2a are attached to a flange 1a formed on the inner periphery of the top of the hollow foundation base 1 which is to be mounted onto a robot body or a fixed base. A first hollow coupling member 3 is rotatably mounted via said bearings 2, 2a, the members having a gear 3a on the outer periphery of the base thereof and a connecting part 3b in the form of a fork at the tip end thereof. Said connecting part 3b of the first of the hollow coupling member 3 is connected to a second coupling member 4 with a universal joint 5 having a center hole in a manner to allow flexion as well as integral rotation, the second coupling member 4 having a hollow base end and a top end formed as a connecting part 4a shaped like a fork. A frame 7 for flexion is mounted on the outer periphery of the second coupling member 4 in a manner to allow relative rotation via a bearing 6.

The second coupling member 4 is connected to a third coupling member 8 by a universal joint 9 having a center hole in a manner to allow free flexion and integral rotation. The third coupling member 8 is made also hollow. To the top end of the third coupling member 8 is connected to a fork-like connecting part 11a of a hand 11 having a pair of gripping members 10, 10a which are actuated to open and close. The above arrangement allows free flexion and integral rotation between two members. A flexible arm 13 which connects the base 1 with the hand 11 thus comprises the first, the second and the third coupling members 3, 4 and 8. A motor 15 having a pinion 14 is mounted inside the base 1 in order to rotate the flexible arm 13 and subsequently the hand 11. The motor drives to rotate the gear 3a on the outer periphery of the base end of the first coupling member 3. In order to flex the flexible arm 13, three hydropneumatic cylinders 16 (only one of them is shown in the figure) are mounted in the base 1. These cylinders 16 are arranged on the periphery at equal intervals, and a rod 16a thereof is movable in reciprocal direction. The tip end of the rod 16a is attached to the base end of the frame 7 of the second coupling member 4 on the outer periphery thereof in a freely rotatable manner. The part beyond the second coupling member 4 therefore can be freely flexed simply by adjusting the length of the three rods 16a. In case two hydropneumatic cylinders are used, they are arranged at positions asymmetrical to each other.

The driving mechanism to open/close the gripping members 10, 10a of a hand will be explained below, beginning with the hand 11.

In the hand 11, each of the gripping members 10, 10a is rotatably attached to the end of two pairs of parallel links 17, 17a. The base ends of the two pairs of parallel links 17, 17a are rotatably attached to the hand 11 and the inner links are fixed on worm wheels 18 respectively. An operating shaft 20 having a worm 19 is arranged between the worm wheels 18 to be held in a rotatable manner with the bearings 21, 21a attached to the hand 11. Therefore, simply by rotating the operating shaft 20, the gripping members 10, 10a on the tip ends of the parallel links 17, 17a can be freely opened or closed via the worm 19 and the worm wheels 18. In order to operate the operating shaft 20 from inside the base 1, the first and the second hand operating shafts 22, 23 are arranged in a dual structure at the center of the flexible arm 13. More particularly, the first hand operating shaft 22 is attached to the center of the first coupling member 3 with bearings 24, 24a in a rotatable manner to penetrate through the spherical bearing 25 attached to the center hole of the universal joint and to reach the inside of the second coupling member 4. The base end of the first hand operating shaft 22, on the other hand, is connected to a motor 26, fixed by a bolt on the gear 3a of the first coupling member 3, and is driven to rotate. The second hand operating shaft 23 is supported with spherical bearings 27, 28 attached to the respective center of the second and the third coupling members 4 and 8 and coupled with the first hand operating shaft 22 by a universal joint 29 on the base thereof. The tip end thereof is coupled by a universal joint 30 to the operative shaft 20 which is attached to the hand on the tip end thereof and which is supported by a spherical bearing 31 mounted in the center hole of the universal joint 12 on the third coupling member 8. An expansion member 23a is provided on an intermediate location of the second hand operating shaft 23 which can absorb changes in the axial length of the arm 13 caused by the flexion but still can transmit revolution by using splines or keys.

When the motor 26 is actuated, therefore, the first and the second hand operating shafts 22, 23 can be rotated separately and independently from the flexible arm 13 to rotate operating shaft 20 of the hand 11.

As the motors 15 and 26 are unavoidably subjected to reaction torque from each other, brakes or other mechanisms are arranged inside to prevent them from reverse revolution.

Figure 3:
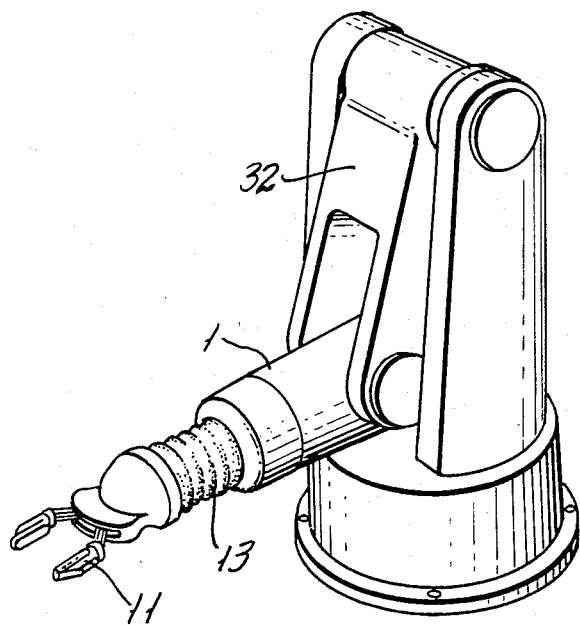
FIG. 3 is a perspective view to show an application of the present invention.

The manipulator of the structure mentioned above is capable rotating the flexible arm 13 and opening/closing of the hand 11 respectively by separately revolving two motors 15 and 26, and further is capable of flexing the flexible arm 13 by expanding/contracting the hydropneumatic cylinder 16. For practical application, the foundation may be mounted to a swingable arm 32 or the like as shown in FIG. 3.

As the number of the hand operating shafts used for the aforementioned embodiment is two and they are coupled with two universal joints, the practically allowable angle is up to 90° because the transmission efficiency will be lowered and the strength of joints will not maintained if the flexion per one universal joint exceeds 45°. If larger flexion angles are desired, the number of hand operating shafts should be increased and the operating shaft for the hand be expandable. At least two actuators are needed for flexion and the number may be increased according to the operability thereof. Respective actuators may be oil pressure motors, pneumatic motors, electric motors, hydropneumatic cylinders etc.

As described referring to the embodiment in the foregoing, the manipulator according to the present invention achieves compact design of arm and wrist members by containing driving mechanisms for flexing and rotation of an arm member and for operating a hand member within the base, thereby allowing application in a narrow location without limiting operation. As the transmission of power is conducted in universal joints, the efficiency is high and transmission stable. As the manipulator according to the present invention does not use wires for flexion, it is free from the influence from expansion or sag thereon, increasing reliability as well as operability. As driving members in the manipulator can be housed together, the wiring, manufacturing and maintenance become easier.

What is claimed is:

1. A manipulator having a base, a hand, and flexible arm means, said flexible arm means comprising: a plurality of hollow coupling members including one adjacent the base, first universal joint means respectively coupling said hollow coupling members to each other so as to allow free flexion and integral rotation thereof, said one hollow coupling member being attached rotatably to said base, first actuator means housed in said base for rotating said one hollow coupling member, a frame mounted rotatably on the hollow coupling member adjacent said one hollow coupling member, a plurality of hand operating shafts including one adjacent said base, spherical bearings attaching said hand operating shafts to said hollow coupling members so as to allow relative rotation therebetween, second universal joint means respectively at intermediate locations of said hollow coupling members for coupling said hand operating shafts to each other, said one hand operating shaft being attached rotatably in said one hollow coupling member, and being connected at one end to an operating shaft for operating said hand, at least another one of said hand operating shafts being expandable, second actuator means attached to said one hollow coupling member for rotating said hand operating shafts, and third actuator means connected to said frame for tilting said frame so as to flex said flexible arm means.

2. The manipulator as claimed in claim 1, wherein said flexible arm means comprises at least three hollow coupling members.

3. The manipulator as claimed in claim 1, wherein said at least one expandable hand operating shaft is attached to the two adjacent hollow coupling members by said spherical bearings respectively.

* * * * *